United States Patent [19]
Vuligonda et al.

[11] Patent Number: 5,599,967
[45] Date of Patent: Feb. 4, 1997

[54] ACETYLENES DISUBSTITUTED WITH A 5 SUBSTITUTED TETRAHYDRONAPHTHYL GROUP AND WITH AN ARYL OF HETEROARYL GROUP HAVING RETINOID-LIKE BIOLOGICAL ACTIVITY

[75] Inventors: Vidyasagar Vuligonda, Irvine; Richard L. Beard, Newport Beach; Alan T. Johnson, Rancho Santa Margarita; Min Teng, Aliso Viejo; Tae K. Song, Long Beach; Roshantha A. Chandraratna, Mission Viejo, all of Calif.

[73] Assignee: Allergan

[21] Appl. No.: 366,169

[22] Filed: Dec. 29, 1994

[51] Int. Cl.⁶ .................................. C07C 69/76
[52] U.S. Cl. .................. 560/48; 560/9; 560/17; 560/43; 562/405; 562/426; 562/427; 562/433; 562/462; 562/490; 564/161; 564/162; 564/163; 564/270
[58] Field of Search .................. 564/161, 162, 564/163, 270; 560/9, 17, 43, 48; 562/405, 462, 490, 426, 427, 433

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/08 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |

(List continued on next page.)

FOREIGN PATENT DOCUMENTS

| | | |
|---|---|---|
| 0098591 | 1/1984 | European Pat. Off. . |
| 0130795 | 1/1985 | European Pat. Off. . |
| 170105 | 2/1986 | European Pat. Off. . |
| 176034 | 4/1986 | European Pat. Off. . |
| 0176033 | 4/1986 | European Pat. Off. . |
| 0176032 | 4/1986 | European Pat. Off. . |
| 0253302 | 1/1988 | European Pat. Off. . |
| 0272921 | 6/1988 | European Pat. Off. . |
| 0284261 | 9/1988 | European Pat. Off. . |
| 0284288 | 9/1988 | European Pat. Off. . |
| 0303186 | 2/1989 | European Pat. Off. . |
| 0303915 | 2/1989 | European Pat. Off. . |
| 0315071 | 5/1989 | European Pat. Off. . |
| 0350846 | 7/1989 | European Pat. Off. . |
| 0412387 | 2/1991 | European Pat. Off. . |
| 0617020 | 9/1994 | European Pat. Off. . |
| 0661258 | 7/1995 | European Pat. Off. . |
| 3316932 | 11/1983 | Germany . |
| 3524199 | 1/1986 | Germany . |
| 3602473 | 7/1987 | Germany . |
| 3708060 | 9/1987 | Germany . |
| 3715955 | 11/1987 | Germany . |
| 2190378 | 11/1987 | United Kingdom . |
| 8500806 | 2/1985 | WIPO . |
| 8504652 | 10/1985 | WIPO . |
| WO9116051 | 10/1991 | WIPO . |
| WO9206948 | 4/1992 | WIPO . |
| 93/21146 | 10/1993 | WIPO . |

OTHER PUBLICATIONS

Eyrolles, L. et al. "Retinoid Antagonists: Molecular Design Based on the Ligand Superfamily Concept" *Med. Chem. Res* (1992) 2:361–367.

Liu, S. S. et al. "Systemic Pharmacokinetics of Acetylenic Retinoids in Rats", *Drug Metabolism and Disposition*, (1990) 18/6:1071–1077.

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.* 43 No. 2, 1978 p. 358.

Conversion of Methyl Ketones into Terminal Acetylenes and (E)–Tri–substituted Olefins of Terpenoid Origin by Ei–ichi, Anthony O. King, and William L. Klima, *J. Org. Chem.* 45 No. 12, 1980 p. 2526.

Sporn et al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

Kagechika et al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

(List continued on next page.)

Primary Examiner—Joseph McKane
Attorney, Agent, or Firm—Gabor L. Szekeres; Robert J. Baran; Martin A. Voet

[57] ABSTRACT

Compounds of the formula

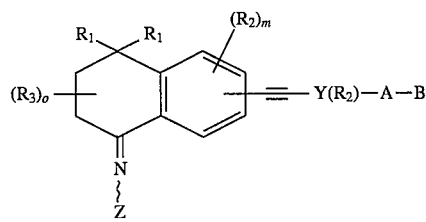

wherein the symbols have the meaning defined in the specification have retinoid-like biological activity.

16 Claims, No Drawings

U.S. PATENT DOCUMENTS

| | | | |
|---|---|---|---|
| 5,068,252 | 11/1991 | Chandraratna | 514/337 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |
| 5,346,895 | 9/1994 | Chandraratna | 514/247 |
| 5,346,915 | 9/1994 | Chandraratna | 514/432 |
| 5,348,972 | 9/1994 | Chandraratna | 514/432 |
| 5,348,975 | 9/1994 | Chandraratna | 514/456 |
| 5,349,105 | 9/1994 | Chandraratna | 564/163 |
| 5,354,752 | 10/1994 | Chandraratna | 514/252 |
| 5,380,877 | 1/1995 | Chandraratna | 549/60 |
| 5,391,753 | 2/1995 | Chandraratna | 546/63 |

OTHER PUBLICATIONS

Synthesis of 2,2'-Diacyl-1,1'-biaryls. Regiocontrolled Protection of . . . by Mervic, et al, *J. Org. Chem.*, No. 45, pp. 4720-4725, 1980.

A Dopamine Receptor Model and its Application in the Design of a New Class of Rigid Pyrrolo [2,3-g]isoquinoline Antipsychotics, Gary L. Olson, et al. *American Chemical Society*, 1981, vol. 24, No. 9, pp. 1026-1031.

6.2.3 Conformational Restriction, Williams, et al., *Drug Discovery and Development*, 1987 The Humana Press, pp. 54-55.

V. Retinoid Structure-Biological Activity Relationships, Chemistry and Biology of Synthetic Retinoids, pp. 324-356, 1990.

Davis et al. *J. Organomettalic Chem* 387 (1990) 381-390.

Effects of 13-Cis-Retinoic Acid, All-Trans-Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792-797.

Organ maintenance of human sebaceous glands: in vitro effects of 13-cis retinoic acid and testosterone, John Ridden, et al., *Journal of Cell Science*, vol. 95, 1990, pp. 125-136.

Characterization of Human Sebaceous Cells In Vitro, Thomas I. Doran, et al., *The Journal of Investigative Dermatology*, vol. 96, No. 3, Mar. 1991.

Synthesis and Evaluation of Stilbene and Dihydrostilbene Derivatives as Potential Anticancer Agents That Inhibit Tubulin Polymerization by Cushman, Mark et al. *J. Med. Chem* 1991, 34, 2579-2588.

Synthesis and Evaluation of New Protein-Tyrosine Kinase Inhibitors. Part 1. Pyridine-Containing Stilbenes and Amides by Cushman, Mark et al. *Bioorganic & Medicinal Chemistry Letters*, vol. 1, No. 4, pp. 211-214, 1991.

Di- and Tri-methoxystyryl Derivatives of Heterocyclic Nitrogen Compounds by Bahner, C. T. et al. Arzneim-Forsch./Drug Res, 31 (I), Nr. 3 (1981).

Retinobenzoic acids. 3. Structure-Activity Relationships of retinoidal Azobenzene-4-carboxylic acids and Stilbene-4-carboxylic acids by H. Kagechika et al., *Journal of Medicinal Chemistry*, 1989, 32, pp. 1098-1108.

ACETYLENES DISUBSTITUTED WITH A 5 SUBSTITUTED TETRAHYDRONAPHTHYL GROUP AND WITH AN ARYL OF HETEROARYL GROUP HAVING RETINOID-LIKE BIOLOGICAL ACTIVITY

1. Field of the Invention

The present invention relates to novel compounds having retinoid-like activity. More specifically, the present invention relates to compounds having an acetylene portion which is substituted with a 5 substituted tetrahydronaphthyl and by a substituted aryl or substituted heteroaryl group having an acid function. The acid function may also be converted to an alcohol, aldehyde or ketone or derivatives thereof, or may be reduced to —CH$_3$.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

U.S. Pat. Nos. 4,740,519 (Shroot et al.), 4,826,969 (Maignan et al.), 4,326,055 (Loeliger et al.), 5,130,335 (Chandraratna et al.), 5,037,825 (Klaus et al.), 5,231,113 (Chandraratna et al.), 5,324,840 (Chandraratna), Published European Patent Application Nos. 0 176 034 A (Wuest et al.), 0 350 846 A (Klaus et al.), 0 176 032 A (Frickel et al.), 0 176 033 A (Frickel et al.), 0 253 302 A (Klaus et al.), 0 303 915 A (Bryce et al.), UK Patent Application GB 2190378 A (Klaus et al.), German Patent Application Nos. DE 3715955 A1 (Klaus et al.), DE 3602473 A1 (Wuest et al., and the articles J. Amer. Acad. Derm. 15: 756–764 (1986) (Sporn et al.), Chem. Pharm. Bull. 33:404–407 (1985) (Shudo et al.), J. Med Chem. 1988 31, 2182–2192 (Kagechika et al.), Chemistry and Biology of Synthetic Retinoids CRC Press Inc. 1990 p 334–335, 354 (Dawson et al.), describe or relate to compounds which include a tetrahydronaphthyl moiety and have retinoid-like or related biological activity. U.S. Pat. No. 4,391,731 (Boller et al.) describes tetrahydronaphthalene derivatives which are useful in liquid crystal compositions. Several co-pending applications and recently issued patents which are assigned to the assignee of the present application, are directed to further compounds having retinoid-like activity.

SUMMARY OF THE INVENTION

The present invention covers compounds of Formula

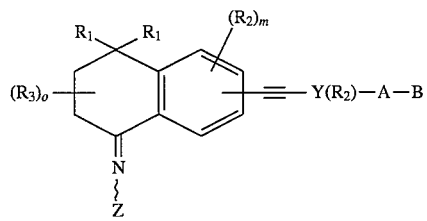

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the tetrahydronaphthalene nucleus;

m is an integer having the value of 0–3;

o is an integer having the value 0–4;

Y is a phenyl group, or heteroaryl selected from a group consisting of pyridyl, thienyl, furyl, pyridazinyl, pyrimidinyl, pyrazinyl, thiazolyl, oxazolyl, and imidazolyl, said groups being optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, $R_{12}$ is lower alkyl, and $R_{13}$ is divalent alkyl radical of 2–5 carbons;

the wavy line represents a single valence bond around which the configuration can be syn or anti, and Z is $OR_1$, $R_1$ is phenyl, benzyl, lower alkyl or lower alkoxy substituted phenyl, $OSi(R_2)_3$, $OCOR_{14}$, $OC(R_{15})(R_{16})XR_{17}$, $N(R_{14})_2$, $NHCON(R_{14})_2$, $NHCSN(R_{14})_2$, where X is O or S; $R_{14}$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$–$C_{10}$-alkylphenyl, naphthyl, $C_1$–$C_{10}$-alkylnaphthyl, phenyl-$C_1$–$C_{10}$alkyl, naphthyl-$C_1$–$C_{10}$alkyl; $R_{15}$ and $R_{16}$ are hydrogen or lower alkyl of 1 to 6 carbons, $R_{17}$ is lower alkyl of 1 to 6 carbons, or $R_{16}$ and $R_{17}$ jointly form a ring having a total of 4 to 5 carbons and the X heteroatom.

In a second aspect, this invention relates to the use of the compounds of Formula 4 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising a compound of Formula 4 in admixture with a pharmaceutically acceptable excipient.

In another aspect, this invention relates to processes for making a compound of Formula 4 which process comprises reacting a compound of Formula 8 with a compound of Formula 9, in the presence of cuprous iodide and $Pd(PQ_3)_2Cl_2$ (Q is phenyl) or a similar complex, or reacting the zinc salt of the compound shown in Formula 8 with a compound of Formula 9 in the presence of $Pd(PQ_3)_4$ (Q is phenyl) or similar complex. In Formula 8 the symbol STHN (substituted tetrahydronaphthyl) represents a tetrahydronaphthalene nucleus which is appropriately substituted to provide the compounds defined in Formula 4 or said tetrahydronaphthalene nucleus is appropriately substituted to provide such precursors of compounds of the Formula 4 from which the target compounds can be readily obtained by organic reactions well known in the art. In Formula 9 $X_1$ is halogen, B' is H, or a protected acid, alcohol, aldehyde, or ketone. In effect, B' is either the desired B group of Formula 4 or B' is a precursor from which the B group can be readily obtained by reactions well known in the art.

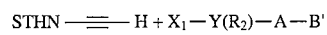

Formula 8        Formula 9

Still further, the present invention relates to such reactions performed on the compounds of Formula 4 which cause transformations of the A–B group or of the substituents on the tetrahydronaphthalene moiety, while the reaction product still remains within the scope of Formula 4.

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B (of Formula 4) is —COOH, this term covers the products derived from treatment of this function with alcohols or thiols preferably with aliphatic alcohols having 1–6 carbons. Where the ester is derived from compounds where B is —$CH_2OH$, this term covers compounds derived from organic acids capable of forming esters including phosphorous based and sulfur based acids, or compounds of the formula —$CH_2OCOR_{11}$ where $R_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some of the compounds of the present invention may have trans and cis (E and Z) isomers. In addition, the compounds of the present invention may contain one or more chiral centers and therefore may exist in enantiomeric and diastereomeric forms. Still further oxime and related compounds of the present invention may exist in syn and anti isomeric forms. The scope of the present invention is intended to cover all such isomers per se, as well as mixtures of cis and trans isomers, mixtures of syn and anti isomers, mixtures of diastereomers and racemic mixtures of enantiomers (optical isomers) as well. In the present application when no specific mention is made of the configuration (cis, trans syn or anti or R or S) of a compound (or of an asymmetric carbon) then a mixture of such isomers, or either one of the isomers is intended. In a similar vein, when in the chemical structural formulas of this application a straight line representing a valence bond is drawn to an asymmetric carbon, then isomers of both R and S configuration, as well as their mixtures are intended. Defined stereochemistry about an asymmetric carbon is indicated in the formulas (where applicable) by a solid triangle showing β configuration, or by a hashed line showing α configuration.

Referring now to the nomenclature used in naming the compounds of the invention and intermediate compounds leading thereto, two different systems for numbering the tetrahydronaphthalene ring are demonstrated as shown by the structural formulas of Compounds F, G and 1. Compound 1 and Compounds F and G are exemplary intermediates utilized in the synthesis of the compounds of the invention. The numbering systems illustrated here will not only be readily apparent to those skilled in the art, but will be readily understood as it is applied in the ensuing description of the compounds of the invention and of intermediates utilized for obtaining the compounds of the invention.

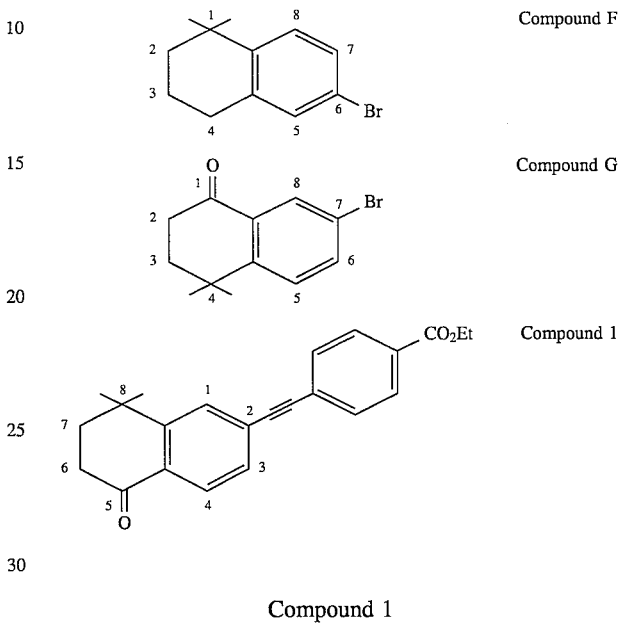

Compound 1

With reference to the symbol Y in Formula 4, the preferred compounds of the invention are those where Y is phenyl, pyridyl, thienyl or furyl. Even more preferred are compounds where Y is phenyl or pyridyl. As far as substitutions on the Y (phenyl) and Y (pyridyl) groups are concerned, compounds are preferred where the phenyl group is 1,4 (para) substituted, and where the pyridine ring is 2,5 substituted. (Substitution in the 2,5 positions in the "pyridine" nomenclature corresponds to substitution in the 6-position in the "nicotinic acid" nomenclature.) In the preferred compounds of the invention there is no optional R$_2$ substituent on the Y group.

The A–B group of the preferred compounds is (CH$_2$)$_n$—COOH or (CH$_2$)$_n$—COOR$_8$ where R$_8$ is defined as above. Even more preferably n is zero and R$_8$ is lower alkyl.

The aromatic portion of the tetrahydronaphthalene moiety is preferably substituted only by the acetylene function. In other words, in the preferred compounds there is no R$_2$ substituent (other than hydrogen). Similarly, in the preferred compounds of the invention there is no R$_3$ substituent (other than hydrogen). The R$_1$ substituent of the compounds of the invention is preferably lower alkyl, and even more preferably methyl.

In the compounds of the invention, the Z group preferably represents OR$_1$, where the R$_1$ group is preferably hydrogen or lower alkyl. Alternatively, Z is preferably 2-tetrahydropyranyloxy. Specific preferred compounds in accordance with Formula 4 and their synthesis are described below in the section of this application titled "Specific Examples". The presently most preferred compounds of the invention in accordance with Formula 4 are indicated in Table 1 below, with reference to Formula 4A. In the Table the compounds are numbered in accordance with the system shown for Compound 1.

TABLE 1

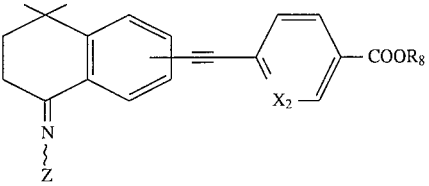

Formula 4A

| Compound No. | Position of Ethynyl Subst. | $X_2$ | $R_8$ | $Z_1$ |
|---|---|---|---|---|
| 19 | 3 | CH | Et | $OH^1$ |
| 20 | 2 | CH | Et | $OH^1$ |
| 21 | 2 | N | Et | $OH^1$ |
| 22 | 2 | CH | Et | $CH_3O^1$ |
| 23 | 2 | CH | Et | $CH_3O^2$ |
| 24 | 2 | CH | Et | $EtO^1$ |
| 25 | 2 | CH | Et | $EtO^2$ |
| 26 | 3 | CH | Et | $CH_3O^1$ |
| 27 | 3 | CH | Et | $CH_3O^2$ |
| 29 | 3 | CH | Et | $EtO^2$ |
| 30 | 3 | CH | Et | 2-tetrahydropyranyloxy$^1$ |
| 31 | 2 | CH | Et | 2-tetrahydropyranyloxy$^1$ |
| 38 | 3 | CH | H | 2-tetrahydropyranyloxy$^1$ |
| 39 | 2 | CH | H | 2-tetrahydropyranyloxy$^1$ |
| 46 | 3 | CH | H | $OH^1$ |
| 47 | 2 | CH | H | $OH^1$ |
| 48 | 2 | N | H | $OH^1$ |
| 49 | 2 | CH | H | $CH_3O^1$ |
| 50 | 2 | CH | H | $CH_3O^2$ |
| 51 | 2 | CH | H | $EtO^1$ |
| 52 | 2 | CH | H | $EtO^2$ |
| 53 | 3 | CH | H | $CH_3O^1$ |
| 54 | 3 | CH | H | $CH_3O^2$ |
| 55 | 3 | CH | H | $EtO^1$ |

$^1$anti
$^2$syn

Modes of Administration

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per mililiter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

Assay of Retinoid-like Biological Activity

The retinoic acid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. Activity of exemplary compounds of the present invention in the above-described ODC assay is disclosed in Table 2 which provides the $IC_{80}$ concentration for the respective exemplary compound. ("$IC_{80}$" is that concentration of the test compound which causes 80% inhibition in the ODC assay. By analogy, "$IC_{60}$, for example, is that concentration of the test compound which causes 60% inhibition in the ODC assay.)

TABLE 2

| Compound # | $IC_{80}$ conc (nmols) |
|---|---|
| 19 | 0.46 |
| 20 | 0.42 |
| 21 | 30* ($IC_{75}$) |
| 22 | 2.50 |
| 23 | 0.35 |
| 24 | 0.29 |

TABLE 2-continued

| Compound # | IC$_{80}$ conc (nmols) |
|---|---|
| 25 | 5.68 |
| 26 | 0.48 |
| 27 | <0.3 |
| 30 | 30* (IC$_{54}$) |
| 31 | 30.32 |
| 38 | 32 |
| 39 | 20.40 |
| 46 | 2.80 |
| 47 | 4.00 |

*the inhibition shown in brackets was attained at this concentration.

SPECIFIC EMBODIMENTS

The compounds of this invention can be made by the synthetic chemical pathways illustrated here. The synthetic chemist will readily appreciate that the conditions set out here are specific embodiments which can be generalized to any and all of the compounds of the invention.

of Formula 12. Compounds of Formula 12 are then coupled with the aromatic or heteroaromatic reagent $X_1$—$Y(R_2)$—A—B' (Formula 9) in the presence of cuprous iodide, a suitable catalyst, typically Pd(PPh$_3$)$_2$Cl$_2$, an acid acceptor, such as triethylamine, under inert gas (argon) atmosphere. Alternatively, a zinc salt (or other suitable metal salt) of the compounds of Formula 12 can be coupled with the reagents of Formula 9 in the presence of Pd(PPh$_3$)$_4$ or similar complex. Typically, the coupling reaction with the reagent $X_1$—$Y(R_2)$—A—B' (Formula 9) is conducted at room or moderately elevated temperature. Generally speaking, coupling between an ethynylaryl derivative or its zinc salt and a halogen substituted aryl or heteroaryl compound, such as the reagent of Formula 9, is described in U.S. Pat. No. 5,264,456, the specification of which is expressly incorporated herein by reference. As it is described below the compounds of Formula 13 are, generally speaking, immediate synthetic precursors to compounds of the invention, or a derivative thereof protected in the B' group, from which the protecting group can be readily removed by reactions well known in the art. The compounds of Formula 13 can

SYNTHESIS
Reaction Scheme 1

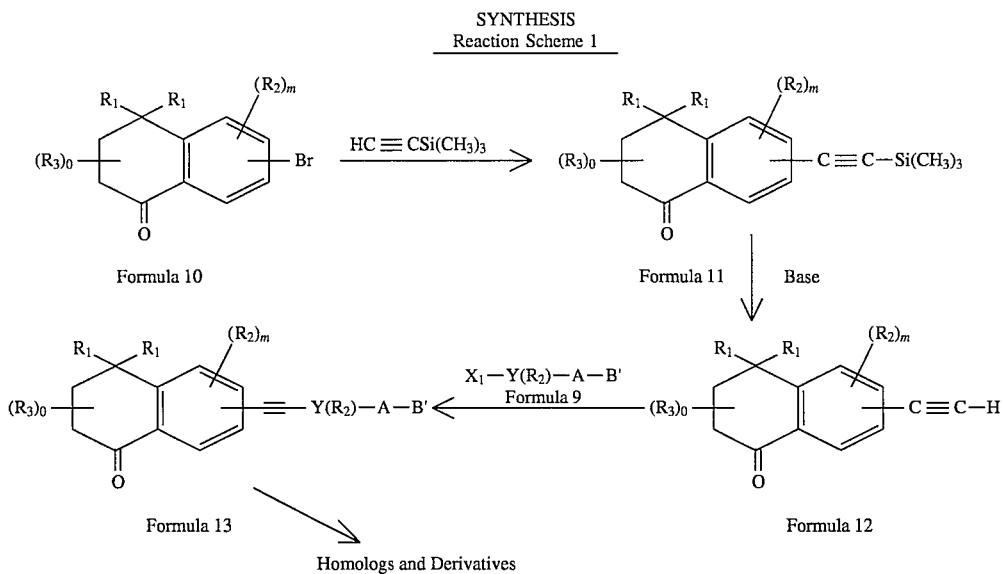

Homologs and Derivatives

Referring now to Reaction Scheme 1 a synthetic route leading to precursors to the compounds of the invention is illustrated. In accordance with this scheme, a 6- or 7-bromo substituted 3,4-dihydro-naphthalen-1(2H)-one (numbering as shown for Compound G) of Formula 10 is the starting material. The compounds of Formula 10 already carry the desired $R_1$, $R_2$ and $R_3$ substituents, as these are defined above in connection with Formula 4. The compounds of Formula 10 are reacted with (trimethylsilyl)acetylene to provide the 6- or 7-(trimethylsilyl)ethynyl- substituted 3,4-dihydro-naphthalen-1(2H)-one compounds of Formula 11. The reaction with (trimethylsilyl)acetylene is typically conducted under heat (approximately 100° C.) in the presence of cuprous iodide, a suitable catalyst, typically having the formula Pd(PPh$_3$)$_2$Cl$_2$, an acid acceptor (such as triethylamine) under an inert gas (argon) atmosphere. Typical reaction time is approximately 24 hours. The 6- or 7-(trimethylsilyl)ethynyl- substituted 3,4-dihydro-naphthalen-1(2H)-one compounds of Formula 11 are then reacted with base (potassium hydroxide or potassium carbonate) in an alcoholic solvent, such as methanol, to provide the 6- or 7-ethynyl substituted 3,4-dihydro-1-naphthalen-1(2H)ones also be converted into further precursors to compounds of the invention by such reactions and transformations which are well known in the art. Such reactions are indicated in Reaction Scheme 1 by conversion into "homologs and derivatives". One such conversion employed for the synthesis of several exemplary compounds of this invention, or to precursors thereof, is saponification of an ester group (when B or B' is an ester) to provide the free carboxylic acid or its salt.

The halogen substituted aryl or heteroaryl compounds of Formula 9 can, generally speaking, be obtained by reactions well known in the art. An example of such compound is ethyl 4-iodobenzoate which is obtainable, for example, by esterification of 4-iodobenzoic acid. Another example is ethyl 6-iodonicotinate which can be obtained by conducting a halogen exchange reaction on 6-chloronicotinic acid, followed by esterification. Even more generally speaking, regarding derivatization of compounds of Formula 13 and/or the synthesis of aryl and heteroaryl compounds of Formula 9 which can thereafter be reacted with compounds of Formula 12 to yield immediate precursors to compounds of the invention, the following well known and published general principles and synthetic methodology can be employed.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

To increase the value of n in the compounds of Formula 9 before affecting the coupling reaction of Reaction Scheme 1 (where such compounds corresponding to Formula 9 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

Compounds of Formula 9, (or other intermediates, or compounds of the invention, as applicable) where A is an alkenyl group having one or more double bonds can be made for example, by synthetic schemes well known to the practicing organic chemist; for example by Wittig and like reactions, or by introduction of a double bond by elimination of halogen from an alpha-halo-arylalkyl-carboxylic acid, ester or like carboxaldehyde. Compounds of Formula 9 (or other intermediates, or of the invention, as applicable) where the A group has a triple (acetylenic) bond can be made by reaction of a corresponding aromatic methyl ketone with strong base, such as lithium diisopropylamide, reaction with diethyl chlorophosphate and subsequent addition of lithium diisopropylamide.

The acids and salts derived from compounds of Formula 13 (or intermediates or compounds of the invention, as applicable) are readily obtainable from the corresponding esters. Basic saponification with an alkali metal base will provide the acid. For example, an ester of Formula 13 may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 9 (or other intermediates or compounds of the invention, as applicable) where B is H can be prepared from the corresponding halogenated aromatic or heteroaromatic compounds, preferably where the halogen is I.

With reference to the coupling reactions of the reagent $X_1$—$Y(R_2)$—A—B' (Formula 9) shown in the foregoing reaction scheme, it is noted that, generally speaking, this coupling reaction can be conducted with 6- or 7- substituted ethynyl compounds which either already have a substituent desired for the present invention in the 5- position or have a precursor suitable for introduction of such desired substituent.

Reaction Scheme 2

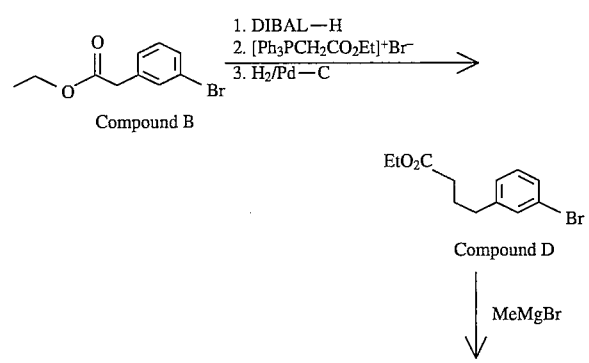

-continued
Reaction Scheme 2

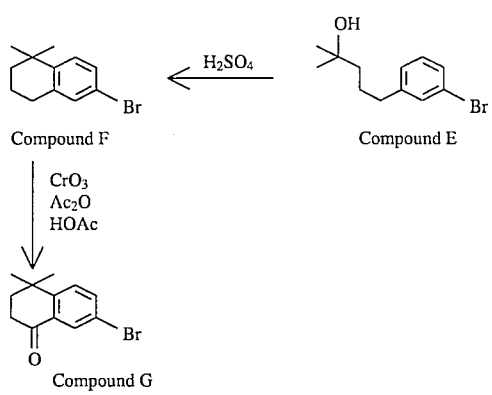

Compound G

In the preferred compounds of the invention the two $R_1$ substituents are methyl, and the $R_2$ and $R_3$ substituents are hydrogen. Reaction Scheme 2 illustrates a synthetic process for preparing 7-bromo-3,4-dihydro-4,4-dimethylnaphthalen-1-one (Compound G) which serves as a starting material for the synthesis of several preferred compounds of the invention. Thus, referring now specifically to Reaction Scheme 2, ethyl 3-bromophenylacetate (Compound B, made by esterification of 3-bromophenylacetic acid) is reduced with diisobutylaluminum hydride (DIBAL—H) to yield (3-bromophenyl)acetaldehyde. (3-Bromophenyl)acetaldehyde is reacted in a Wittig reaction with (carbethoxymethylene)triphenylphosphorane to provide a mixture of E and Z ethyl 4-(3-bromophenyl)but-2-enoates. The latter compounds are hydrogenated to yield ethyl 4-(3-bromophenyl)butanoate (Compound D). Compound D is reacted with the Grignard reagent derived from methylbromide to give the tertiary alcohol 5-(3-bromophenyl)-2-methylpentan-2-ol (Compound E) (It should be apparent to those skilled in the art, that the choice of the Grignard reagent used in this reaction step determines the nature of the $R_1$ substituent in the resulting compounds of the invention.) Compound E is then treated with acid to cyclize it and to form 6-bromo-1,2,3,4-tetrahydro-1,1-dimethylnaphthalene (Compound F). Compound F is oxidized with chromium trioxide to yield 7-bromo-3,4-dihydro-4,4-dimethylnaphthalen-1(2H)-one (Compound G). Compound G is covered by Formula 10 and in accordance with Reaction Scheme 1 serves as a starting material in the synthesis of several preferred compounds of the invention.

6-Bromo-3,4-dihydro-4,4-dimethylnaphthalen-1(2H)one (Compound H) is isomeric with Compound G, and can be obtained, starting with ethyl (4-bromophenyl)acetate, in accordance with the sequence of reactions illustrated in Reaction Scheme Z for Compound G. 6-Bromo-3,4-dihydro-4,4-dimethylnaphthalen-1(2H)-one (Compound H) can also be obtained in accordance with the published literature procedure: Mathur et al. Tetrahedron, 41, 1509–1516 (1985). Compound H is also covered by Formula 10 and serves as a starting material in the synthesis of several preferred compounds of the invention.

Starting materials for the synthetic route outlined in Reaction Scheme 1 where the $R_2$ and/or $R_3$ groups are other than hydrogen, can be obtained similarly to the synthesis of the starting materials demonstrated in Reaction Scheme 2, and/or by introducing the $R_2$ by a Friedel-Crafts or like reaction into the aromatic portion of the tetrahydronaphthalene nucleus.

Reaction Scheme 3

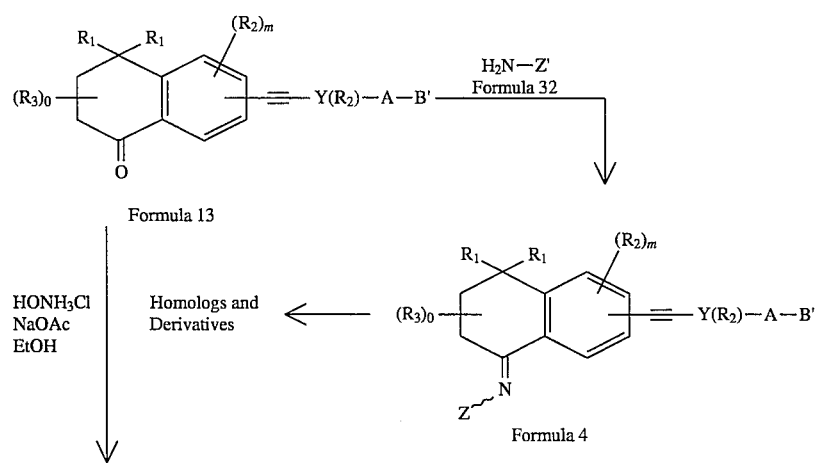

-continued
Reaction Scheme 3

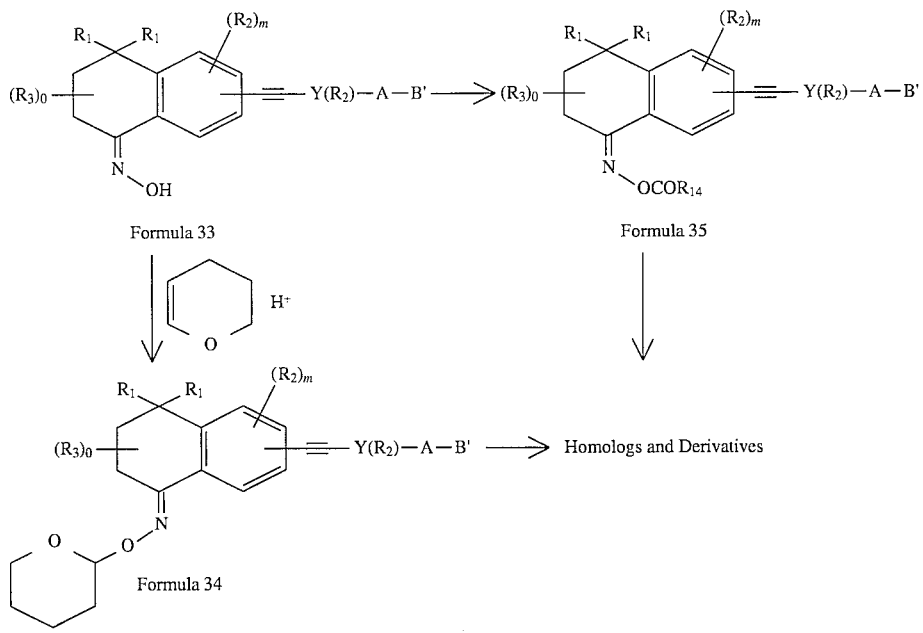

Compounds of Formula 4 are preferably synthesized from the 5-oxo-2- or 3- (aryl or heteroaryl)ethynyl 5,6,7,8-tetrahydronaphthalene compounds of Formula 13 (numbering as exemplified for Compound 1) as is illustrated in Reaction Scheme 3. Thus, the 5-oxo compounds of Formula 13 are reacted with a reagent of the formula $H_2N$—Z (Formula 32), where Z is defined as in connection with Formula 4, to yield compounds of Formula 4. Those skilled in the art will recognize that when the reagent $H_2N$—Z is $NH_2OH$ or its salt, then the reaction is the formation of an oxime. These oximes are readily formed by reacting the compounds of Formula 13 with hydroxylamine hydrochloride in a polar solvent, such as a lower alkanol, in the presence of a buffering agent, such as sodium acetate. The reaction can be conducted under similar conditions with a reagent of the formula $NH_2OR_1$ or its salt (such as methoxylamine hydrochloride or ethoxylamine hydrochloride) to yield compounds of Formula 4 where Z is $OR_1$ ($R_1$ is defined as in connection with Formula 4). When the reagent $H_2N$—Z is a primary amine (Z is $R_1$, phenyl or benzyl) then the reaction between the compounds of Formula 13 and the primary amine is the formation of an imine. The latter reaction is usually conducted in a polar (alcoholic) solvent. Further reagents, in accordance with Formula 32 are those where Z is $NHCON(R_{14})_2$ (formation of semicarbazone), $NHCSN(R_{14})_2$ (formation of thiosemicarbazone) and $N(R_{14})_2$ (formation of a hydrazone). (The symbol $R_{14}$ is defined as in connection with Formula 4.) The semicarbazones, thiosemicarbazones and hydrazones corresponding to Formula 4 can be prepared under conditions which are well known in the art for the formation of such derivatives of ketone compounds. Usually these conditions are similar to the conditions leading to the oximes of compounds of Formula 13. Typically, the hydrochloride salt of of the reagent (semicarbazide, thiosemicarbazide or hydrazide) is reacted with the compound of Formula 13 in an alcoholic solvent, in the presence of sodium acetate.

Referring still to Reaction Scheme 3 synthesis of O-(2-tetrahydropyranyl)oxime derivatives of the structure shown by Formula 34 is illustrated. To obtain these compounds, an oxime derivative of the Formula 33 is first prepared in accordance with the reaction described above. The oxime derivative of Formula 33 is thereafter reacted with 3,4-dihydro-2-H-pyran (DHP) in an inert solvent (such as dichloromethane) in the presence of acid, typically pyridinium p-tolunesulfonate (PPTS). This reaction is typically conducted in the cold, or at ambient temperature. The resulting product of Formula 34 is usually isolated by chromatography. Compounds of Formula 4 where the Z group represents $OC(R_{15})(R_{16})XR_{17}$ other than tetrahydropyranyl, (X is O or S so that the reagent is for example tetrahydrothiopyranyl) can be prepared in reaction steps analogous to the ones described above for the preparation of compounds of Formula 34. The oxime derivatives of Formula 33 can also be reacted with an appropriate reagent (such as an acyl chloride $R_{14}COCl$) to introduce the $R_{14}CO$ group, to provide the compounds of Formula 35. The compounds of Formula 4, 33, 34 and 35 can be converted into further homologs and derivatives as is described above for compounds of Formula 13 and shown in Reaction Scheme 3.

In addition to the synthetic steps shown in Reaction Scheme 3, the compounds of Formula 4 can also be obtained, generally speaking, by first forming an oxime, alkoxyoxime, imine, hydrazone, semicarbazone etc. from the ketone compounds of Formula 10 (see Reaction Scheme 1) and thereafter performing the synthetic steps of replacing the 6 or 7-bromo substituents in the resulting oximes, alkoxyoximes etc. with an ethynyl group and subsequently coupling the ethynyl compounds with the reagent $X_1$—$Y(R_2)$—A—B' (Formula 9).

SPECIFIC EXAMPLES

Ethyl (4-bromophenyl)acetate (Compound A)

A solution of 43 g (200 mmol) of 4-bromophenylacetic acid and 0.2 g of conc. $H_2SO_4$ in 470 ml of ethanol was refluxed for 16 hours. The reaction mixture was cooled to ambient temperature, stirred with 6 g of solid $K_2CO_3$ for 30 minutes and then filtered. The filtrate was concentrated in vacuo, diluted with $Et_2O$ (200 ml), washed with 10% aqueous $NaHCO_3$ (10 ml) and brine (10 ml), dried over $MgSO_4$ and concentrated in vacuo to give the title compound as a colorless oil. PMR ($CDCl_3$): δ 1.25 (3H, t, J=7.0 Hz), 3.56 (2H, s), 4.15 (2H, q, J=7.0 Hz), 7.16 (2H, d, J=8.4 Hz), 7.45 (2H, d, J=8.4 HZ).

Ethyl (3-bromophenyl)acetate (Compound B)

Employing the same general procedure as for the preparation of ethyl (4-bromophenyl)acetate (Compound A), 100 g (463 mmol) of 3-bromophenylacetic acid was converted into the title compound (yellow oil) using 2 g of conc. $H_2SO_4$ and 500 ml of ethanol.

PMR ($CDCl_3$): δ 1.26 (3H, t, J=7.0 Hz), 3.56 (2H, s), 4.16 (2H, q, J=7.0 Hz), 7.16–7.26 (2H, m), 7.38–7.46 (2H, m).

Ethyl 4-(4-bromophenyl)butanoate (Compound C)

To a cold solution (−78° C.) of 15 g (62 mmol) of ethyl (4-bromophenyl)acetate (Compound A) in 150 ml of $CH_2Cl_2$ was added dropwise (over a span of 1 hour) 65 ml (65 mmol) of diisobutylaluminum hydride (DIBAL—H, 1M solution in hexane). After the DIBAL—H addition was complete, the reaction was stirred at −78° C. for an additional hour. The reaction was quenched by the dropwise addition of methanol (10 ml), followed by water (10 ml) and 10% HCl (40 ml). The mixture was then warmed to 0° C., stirred for 10 minutes and then washed with water (15 ml), 10% aqueous $NaHCO_3$ (10 ml) and brine (10 ml). The organic phase was dried over $MgSO_4$ and the solvent distilled off at ambient temperature to give crude (4-bromophenyl)acetaldehyde. To a cold solution (0° C.) of this crude aldehyde in 150 ml of $CH_2Cl_2$ was added a solution of 26 g (74.6 mmol) of (carbethoxymethylene)triphenylphosphorane in 50 ml of $CH_2Cl_2$. The mixture was stirred for 16 hours, concentrated in vacuo and purified by flash chromatography (silica, 10% EtOAc-hexane) to give ethyl 4-(4-bromophenyl)but-2-enoate as a mixture of E:Z isomers. This isomeric mixture was dissolved in 150 ml of EtOAc and hydrogenated over 1 g of 10% Pd/C for 6 hours. The catalyst was filtered off and the filtrate concentrated in vacuo to give the title compound as a white solid.

PMR ($CDCl_3$): δ 1.26 (3H, t, J=7.1 Hz), 1.88–1.99 (2H, m), 2.31 (2H, t, J=7.5 Hz), 2.61 (2H, t, J=7.5 Hz), 4.28 (2H, q, J=7.1 Hz), 7.05 (2H, d, J=8.4 Hz), 7.40 (2H, d, J=8.4 Hz).

Ethyl 4-(3-bromophenyl)butanoate (Compound D)

Employing the same general multistep preparation as for ethyl 4-(4-bromophenyl) butanoate (Compound C), 60 g (246 mmol) of ethyl (3-bromophenyl)acetate (Compound B) was converted into the title compound (oil) using 255 ml (255 mmol) of diisobutylaluminum hydride (DIBAL—H, 1M in hexane), 85.8 g (250 mmol) of (carbethoxymethylene) triphenylphosphorane and 1.7 g of 10% Pd/C.

PMR ($CDCl_3$): δ 1.26 (3H, t, J=7.1 Hz), 1.89–2.00 (2H, m), 2.31 (2H, t, J=7.5 Hz), 2.63 (2H, t, J=7.2 Hz), 4.15 (2H, q, J=7.1 Hz), 7.10–7.35 (4H, m).

5-(3-bromophenyl)-2-methylpentan-2-ol (Compound E)

To a cold solution (0° C.) of 17 g (63 mmol) of ethyl 4-(3-bromophenyl) butanoate (Compound D) in 40 ml of THF was added 63 ml (189 mmol) of methylmagnesium bromide (3.0M solution in THF). The reaction was stirred at 0° C. for 2 hours, quenched by the slow addition of ice cold water (30 ml) followed by 10% HCl (30 ml) and then extracted with $Et_2O$ (4×60 ml). The combined organic layer was washed with 10% aqueous $NaHCO_3$ (10 ml), water (10 ml) and brine (10 ml), dried over $MgSO_4$ and concentrated in vacuo. Purification by Kugelrohr distillation gave the title compound as a colorless oil.

PMR ($CDCl_3$): δ 1.20 (6H, s), 1.43–1.55 (2H, m), 1.62–1.78 (2H, m), 2.60 (2H, t, J=6.0 Hz), 7.10–7.41 (4H, m).

6-Bromo-1,2,3,4-tetrahydro-1,1-dimethylnaphthalene (Compound F)

15.0 g (58.3 mmol) of 5-(3-bromophenyl)-2-methyl-pentan-2-ol (Compound E) was cooled to 0° C. and then 2.8 ml of conc. $H_2SO_4$ was added. The mixture was stirred for 2.5 hours, diluted with water (20 ml) and extracted with $Et_2O$ (3×40 ml). The combined organic layers were washed with water, sat. aqueous $NaHCO_3$ and brine, dried over $MgSO_4$ and concentrated in vacuo. Purification by Kugelrohr distillation gave the title compound as a colorless oil.

PMR ($CDCl_3$): δ 1.25 (6H, s), 1.61–1.66 (2H, m), 1.74–1.82 (2H, m), 2.73 (2H, t, J=6.0 Hz), 7.16–7.26 (3H, m).

7-Bromo-3,4-dihydro-4,4-dimethylnaphthalen-1(2H)-one (Compound G)

To a cold mixture (0° C.) of 209 g (200 mmol) of chromium trioxide, 100 ml (1.06 mol) of acetic anhydride and 200 ml (3.5 mol) of acetic acid was added a solution of 10 g (41.8 mmol) of 6-bromo-1,2,3,4-tetrahydro-1,1-dimethylnaphthalene (Compound F) in 125 ml of benzene. The reaction mixture was stirred for 1 hour, quenched with ice cold water and extracted with $Et_2O$ (3×100 ml). The organic layer was dried over $MgSO_4$, concentrated in vacuo, and purified by column chromatography (silica, 10% EtOAc-hexane) to give the title compound as a white solid.

PMR ($CDCl_3$): δ 1.28 (6H, s), 2.01 (2H, t, J=6.0 Hz), 2.72 (2H, t, J=6.0Hz), 7.31 (1H, d, J=9.0 Hz), 7.61 (1H, dd, J=3.0, 9.0 Hz), 8.11 (1H, d, J=3.0 Hz).

6-Bromo-3,4-dihydro-4,4-dimethylnaphthalen-1(2H)-one (Compound H)

Employing a published procedure (Mathur, N.C.; Snow, M.S. ; Young, K. M.; and Pincock, J. A. Tetrahedron, 41, 1509–1516 (1985)), ethyl 4-(4-bromophenyl)butanoate (Compound C) was converted into the title compound. Alternatively, the title compound can be obtained using similar reactions that were used to convert ethyl 4-(3-bromophenyl)butanoate (Compound D) into 7-bromo-3,4-dihydro-4,4-dimethylnaphthalen- 1(2H)-one (Compound G).

6-Ethynyl,3,4-dihydro-4,4-dimethylnaphthalen-1(2H)-one (Compound K)

To a solution (flushed for 15 minutes with a stream of argon) of 13.55 g (53.8 mmol) of 6-bromo-3,4-dihydro-4,4-dimethylnaphthalen-1(2H)-one (Compound H) in 280 ml of triethylamine was added 1.87 g (2.66 mmol) of bis(triphenylphosphine)palladium(II) chloride and 0.53 g (2.66 mmol) of cuprous iodide. The solution mixture was flushed with argon for 5 minutes and then 100 ml (938.7 mmol) of (trimethylsilyl)acetylene was added. The reaction mixture was sealed in a pressure tube and placed in a preheated oil bath (100° C.) for 24 hours. The reaction mixture was then filtered through Celite, washed with Et$_2$O and the filtrate concentrated in vacuo to give crude 6-(trimethylsilyl)ethynyl-3,4-dihydro-4,4-dimethylnaphthalen-1(2H)-one. To a solution of this crude TMS-acetylenic compound in 50 ml of methanol was added 2.8 g (20.3 mmol) of K$_2$CO$_3$. The mixture was stirred for 8 hours at ambient temperature and then filtered. The filtrate was concentrated in vacuo, diluted with Et$_2$O (100 ml), washed with water (10 ml), 10% HCl (10 ml) and brine (10 ml), dried over MgSO$_4$ and concentrated in vacuo. Purification by column chromatography (silica, 10% EtOAc-hexane) yielded the title compound as a white solid.

PMR (CDCl$_3$): δ 1.38 (6H, s), 2.01 (2H, t, J=7.1 Hz), 2.72 (2H, t, J=7.1 Hz), 3.24 (1H, s), 7.39 (1H, dd, J=1.5, 8.1 Hz), 7.54 (1H, d, J=1.5 Hz), 7.91 (1H, d, J=8.1 Hz).

7-Ethynyl-3,4-dihydro-4,4-dimethylnaphthalen-1(2H)-one (Compound L)

Employing the same general procedure as for the preparation of 6-ethynyl-3,4-dihydro-4,4-dimethyl-naphthalen-1(2H)-one (Compound K), 7 g (27.6 mmol) of 7-bromo-3,4-dihydro-4,4-dimethylnaphthalen-1(2H)-one (Compound G) was converted into the title compound using 39 ml (36.6 mmol) of (trimethylsilyl)acetylene, 0.97 g (1.3 mmol) of bis(triphenylphosphine)palladium(II) chloride, 0.26 g (1.3 mmol) of cuprous iodide and 0.6 g (4.3 mmol) of K$_2$CO$_3$.

PMR (CDCl$_3$): δ 1.39 (6H, s), 2.02 (2H, t, J=7.0 Hz), 2.73 (2H, t, J=7.0 Hz), 3.08 (1H, s), 7.39 (1H, d, J=8.2 Hz), 7.61 (1H, dd, J=1.8 , 8.2 Hz), 8.14 (1H, d, J=9 1.8 Hz).

Ethyl-4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated NaHCO$_3$ and saturated NaCl solutions and dried (MgSO$_4$). Solvent was then removed in vacuo and the residue Kugelrohr distilled (100 degrees C.; 0.55 mm) to give the title compound as a colorless oil, PMR (CDCl$_3$): δ 1.42 (3H, t, J~7 Hz), 4,4 (2H, q, J~7 Hz), 7.8 (4H).

Ethyl 6-chloronicotinate

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and the residue subjected to flash chromatography to give the title compound as a low-melting white solid. PMR (CDCl$_3$): δ 1.44 (3H, t, J~6.2 Hz) 4.44 (2H, q, J~4.4 Hz), 7.44 (1H, d, J~8.1 Hz), 8.27 (1H, dd, J~8.1 Hz, 3 Hz), 9.02 (1H, d, J~3 Hz).

6-Iodonicotinic acid

To 27.97 g (186.6 mmol) of sodium iodide cooled to −78° C. was added 121.77 g (71.6 ml, 952.0 mmol) of hydriodic acid (57 wt %). The reaction mixture was allowed to warm slightly with stirring for 5 minutes, and then 30.00 g (190.4 mmol) of 6-chloronicotinic acid was added. The resulting mixture was allowed to warm to room temperature with stirring and then heated at 120°–125° C. in an oil bath for 42 hours. A dark brown layer formed above the yellow solid material. The reaction mixture was allowed to cool to room temperature and then poured into acetone (chilled to 0° C.). The resultant yellow solid was collected by filtration, washed with 200 ml of 1N NaHSO$_3$ solution, and dried in high vacuum (3 mm Hg) to give the title compound as a pale yellow solid.

PMR (DMSO-d$_6$): δ 7.90 (1H, dd, J=8.1, 2 Hz), 7.99 (1H, d, J=8.1 Hz), 8.80 (1H, d, J=2.Hz).

Ethyl 6-iodonicotinate

To a suspension of 23.38 g (94.2 mmol) of 6-iodonicotinic acid in 100 ml of dichloromethane was added a solution of 19.86 g (103.6 mmol) of 1-(3-dimethylamino-propyl)-3-ethylcarbodiimide hydrochloride in 250 ml of dichloromethane. To this suspension was added 12.40 g (15.8 ml, 269.3 mmol) of ethanol (95%) and 1.15 g (9.4 mmol) of 4-dimethylaminopyridine. The resulting solution mixture was then heated at 50° C. in an oil bath for 24.5 hours, concentrated in vacuo, partitioned between 200 ml of water and 250 ml of ethyl ether, and the layers were separated. The aqueous phase was washed with 2×150 ml portions of ethyl ether. All organic phases were combined, washed once with 75 ml of brine solution, dried over MgSO$_4$, filtered and concentrated in vacuo to a yellow solid. Purification by flash chromatography (silica, 10% ethyl acetate in hexane) yielded the title compound as a white solid.

PMR (CDCl$_3$): δ 1.41 (3H, t, J=7.1 Hz), 4.41 (2H, q, J=7.1 Hz), 7.85 (1H, d, J=8.2 Hz), 7.91 (1H, dd, J=8.2, 2.1 Hz), 8.94 (1H, d, J=2.1 Hz).

Ethyl 4-[(5,6,7,8-tetrahydro-8,8-dimethyl-5-oxonaphth-2-yl)ethynyl]benzoate (Compound 1)

To a solution of 8.8 g (47.8 mmol) of 6-ethynyl-1,2,3,4-tetrahydro-4,4-dimethylnaphthalen-1-one (Compound K) flushed for 15 minutes with a stream of argon, and 13.2 g (47.8 mmol) of ethyl 4-iodobenzoate in 200 ml of triethylamine was added 1.1 g (1.6 mmol) of bis(triphenylphosphine)palladium(II) chloride and 0.30 g (1.6 mmol) of cuprous iodide. The solution mixture was flushed with argon for 5 minutes and then stirred at ambient temperature for 18 hours. The reaction mixture was filtered through Celite and the filtrate concentrated in vacuo. Purification by flash chromatography (silica, 10% EtOAc-hexane) yielded the title compound as a white solid.

PMR (CDCl$_3$): δ 1.41 (3H, t, J=7.2 Hz), 1.43 (6H, s), 2.04 (2H, t, J=7.0 Hz), 2.75 (2H, t, J=7.0 Hz), 4.40 (2H, q, J=7.2 Hz), 7.46 (1H, dd, J=1.5, 8.1 Hz), 7.60 (1H, d, J=1.5 Hz), 7.63 (2H, d, J=8.4 Hz), 8.01 (1H, d, J=8.1 Hz), 8.05 (2H, d, J=8.4 Hz).

Ethyl 4-[(5,6,7,8-tetrahydro-8,8-dimethyl-5-oxonaphth-3-yl)ethynyl]benzoate (Compound 2)

Employing the same general procedure as for the preparation of ethyl 4-[(5,6,7,8-tetrahydro-8,8-dimethyl- 5-oxonaphth-2-yl) ethynyl]benzoate (Compound 1), 4 g (21.7 mmol) of 7-ethynyl-3,4-dihydro-4,4-dimethyl-naphthalen-1(2H)-one (Compound L) was converted into the title compound using 6 g (21.7 mmol) of ethyl 4-iodobenzoate, 5 g (7.2 mmol) of bis(triphenylphosphine)palladium(II) chloride and 1.4 g (7.2 mmol) of cuprous iodide.

PMR (CDCl$_3$): δ 1.41 (3H, t, J=7.2 Hz), 1.41 (6H, s), 2.04 (2H, t, J=6.5 Hz), 2.76 (2H, t, J=6.5 Hz), 4.40 (2H, q, J=7.2 Hz), 7.44 (1H, d, J=8.2 Hz), 7.59 (2H, d, J=8.4 Hz), 7.68 (1H, dd, J=1.8, 8.2 Hz), 8.04 (2H, d, J=8.4 Hz), 8.15 (1H, d, J=1.8 Hz).

Ethyl 6[(5,6,7,8-tetrahydro-8,8-dimethyl-5-oxonaphth-3-yl)ethynyl]nicotinate (Compound 3)

Employing the same general procedure as for the preparation of ethyl 4-[(5,6,7,8-tetrahydro-8,8-dimethyl-5-oxonaphth-2-yl) ethynyl]benzoate (Compound 1), 606 mg (3.48 mmol) of 7-ethynyl-3,4-dihydro-4,4-dimethyl-naphthalen-1(2H)-one (Compound K) was converted into the title compound using 964 mg (3.48 mmol) of ethyl 6-iodonicotinate, 122 mg (0.17 mmol) of bis(triphenylphosphine)palladium(II) chloride and 9.5 mg (0.17 mmol) of cuprous iodide.

PMR (CDCl$_3$): δ 1.41 (6H, s), 1.43 (3H, t, J=7.1 Hz), 2.05 (2H, t, J=7.1 Hz), 2.76 (2H, t, J=7.1 Hz), 4.43 (2H, q, J=7.1 Hz), 7.46 (1H, d, J=8.2 Hz), 7.60 (1H, d, J=7.8 Hz), 7.75 (1H, dd, J=1.9, 8.2 Hz), 8.27 (1H, d, J=1.9 HZ), 8.30 (1H, dd, J=2.0, 7.8 Hz), 9.22 (1H, br s).

Ethyl 6-[(5,6,7,8-tetrahydro-8,8-dimethyl-5-oxonaphth2-yl)ethynyl]nicotinate (Compound 5)

Employing the same general procedure as for the preparation of ethyl 4-[5,6,7,8-tetrahydro-8,8-dimethyl-5-oxonaphth-2-yl)ethynyl]benzoate (Compound 1), 422 mg (2.1 mmol) of 6-ethynyl-3,4-dihydro-4,4-dimethyl-naphthalen-1(2H)-one (Compound L) was converted into the title compound using 202 mg (0.73 mmol) of ethyl 6-iodonicotinate, 168 mg (0.24 mmol) of bis(triphenylphosphine)palladium(II) chloride and 45.7 mg (0.24 mmol) of cuprous iodide.

PMR (CDCl$_3$): δ 1.40 (6H, s), 1.42 (3H, t, J=7.1 Hz), 2.04 (2H, t, J=6.0 Hz), 2.74 (2H, t, J=6.0 Hz), 4.43 (2H, q, J=7.1 Hz), 7.51 (1H, d, J=8.4 Hz), 7.63 (1H, d, J=8.4 Hz), 7.70 (1H, s), 8.01 (1H, d, J=8.1 Hz), 8.30 (1H, d, J=8.1 Hz), 9.22 (1H, s).

4-[5,6,7,8-tetrahydro-8,8-dimethyl-5-oxonaphth-2-yl)ethynyl]benzoic acid (Compound 7)

To a suspension of 0.30 g (0.87 mmol) of ethyl 4-[(5,6,7,8-tetrahydro-8,8-dimethyl-5-oxonaphth-2-yl)ethynyl]benzoate (Compound 1) in 4 ml of THF and 2 ml of ethanol was added 2 ml (2 mmol) of LiOH (1N aqueous solution). The reaction mixture was stirred at room temperature for 4 hours, concentrated in vacuo to near dryness, partitioned between EtOAc and 1 ml of water and acidified to pH 4 with 10% HCl. The aqueous layer was extracted with EtOAc and then the organic layer was dried over Na$_2$SO$_4$ and concentrated in vacuo to give the title compound as a light yellow solid.

PMR (DMSO-d$_6$): δ 1.39 (6H, s), 1.98 (2H, t, J=7.0 Hz), 2.70 (2H, t, J=7.0 Hz), 7.54 (1H, dd, J=1.5, 8.1 Hz), 7.73 (2H, d, J=8.4 Hz), 7.77 (1H, d, J=1.5 Hz), 7.90 (1H, d, J=8.1 Hz), 8.00 (2H, d, J=8.4 Hz).

4-[(5,6,7,8-tetrahydro-8,8-dimethyl-5-oxonaphth-3yl)ethynyl]benzoic acid (Compound 8)

Employing the same general procedure as for the preparation of 4-[(5,6,7,8-tetrahydro-8,8-dimethyl-5-oxonaphth-2-yl)ethynyl]benzoic acid (Compound 7), 500 mg (1.45 mmol) of ethyl 4-[(5,6,7,8-tetrahydro-8,8-dimethyl-5-oxonaphth-3-yl)ethynyl]benzoate (Compound 2) was converted into the title compound using 4 ml (4 mmol) of LiOH (1N aqueous solution).

PMR (DMSO-d$_6$): δ 1.37 (6H, s), 1.99 (2H, t, J=6.9 Hz), 2.71 (2H, t, J=6.9 Hz), 7.64 (1H, d, J=8.2 Hz), 7.70 (2H, d, J=8.3 Hz), 7.80 (1H, dd, J=2.0, 8.2 Hz), 7.98 (3H, m).

Ethyl 4-[5,6,7,8-tetrahydro-8,8-dimethyl-5-(oxime)naphth-3-yl)ethynyl]benzoate (Compound 19)

A solution of 500 mg (1.44 mmol) of ethyl 4-[(5,6,7,8-tetrahydro-8,8-dimethyl-5-oxonaphth-3-yl)ethynyl]benzoate (Compound 2), 110 mg (1.6 mmol) of hydroxylamine hydrochloride and 431 mg (3.2 mmol) of sodium acetate in 5 ml of EtOH was stirred at ambient temperature for 16 hours. The mixture was diluted with water (10 ml) and extracted with EtOAc (3×30 ml). The organic layer was washed with water (5 ml) and brine (10 ml), dried over MgSO$_4$ and concentrated in vacuo. Recrystallization from EtOAc-hexane yielded the title compound as a white solid.

PMR (CDCl$_3$): δ 1.30 (6H, s), 1.41 (3H, t, J=7.2 Hz), 1.75 (2H, t, J=7.0 Hz), 2.90 (2H, t, J=7.0 Hz), 4.39 (2H, q, J=7.2 Hz), 7.35 (1H, d, J=8.1 Hz), 7.48 (1H, d, J=8.1 Hz), 7.57 (2H, d, J=8.2 Hz), 8.02 (2H, d, J=8.2 Hz), 8.08 (1H, d, J=1.5 Hz).

Ethyl 4-[5,6,7,8-tetrahydro-8,8-dimethyl-5-(oxime)naphth-2-yl)ethynyl]benzoate (Compound 20)

Employing the same general procedure as for the preparation of ethyl 4-[(5,6,7,8-tetrahydro-8,8 -dimethyl-5-(oxime)naphth-3-yl )ethynyl]benzoate (Compound 19), 346 mg (1.0 mmol) of ethyl 4-[(5,6,7,8-tetrahydro-8,8-dimethyl -5-oxonaphth-2 -yl)ethynyl]benzoate (Compound 1) was converted into the title compound using 125 mg (1.8 mmol) of hydroxylamine hydrochloride and 485 mg (3.6 mmol) of sodium acetate trihydrate.

PMR (CDCl$_3$): δ 1.34 (6H, s), 1.42 (3H, t, J=7.1 Hz), 1.78 (2H, t, J=6.2 Hz), 2.89 (2H, t, J=6.2 Hz), 4.40 (2H, q, J=7.1 Hz), 7.37 (1H, dd, J=1.9, 7.9 Hz), 7.56 (1H, d, J=1.9 Hz), 7.60 (2H, d, J=8.2 Hz), 7.91 (1H, d, J=7.9 Hz), 8.04 (2H, d, J=8.2 Hz).

Ethyl 6-[5,6,7,8-tetrahydro-8,8-dimethyl-5-(oxime)naphth-2-yl)ethynyl]nicotinate (Compound 21)

Employing the same general procedure as for the preparation of ethyl 4-[(5,6,7,8-tetrahydro-8,8-dimethyl-5-(oxime)naphth-3-yl)ethynyl]benzoate (Compound 19), 200 mg (0.58 mmol) of ethyl 6-[(5,6,7,8-tetrahydro-8,8-dimethyl-5-oxonaphth-2-yl)ethynyl]nicotinate (Compound 5) was converted into the title compound using 126 mg ( 1.8 mmol ) of hydroxylamine hydrochloride and 286 mg (2.1 mmol) of sodium acetate trihydrate.

PMR (CDCl$_3$): δ 1.31 (6H, s), 1.43 (3H, t, J=7.1 Hz), 1.77 (2H, t, J=7.0 Hz), 2.88 (2H, t, J=7.0 Hz), 4.44 (2H, q, J=7.1 Hz), 7.41 (1H, d, J=8.1 Hz), 7.62 (1H, d, J=8.5Hz), 7.65 (1H, s), 7.90 (1H, d, J=8.1 Hz), 8.31 (1H, dd, J=2.2, 8.5 Hz), 9.23 (1H, d, J=2.2 Hz).

Ethyl 4-[(5,6,7,8-tetrahydro-8,8-dimethyl-5-anti-(O-methyl oxime)naphth-2-yl)ethynyl]benzoate (Compound 22) and Ethyl 4-[(5,6,7,8-tetrahydro-8,8-dimethyl-5-syn-(O-methyl oxime)naphth-2-yl)ethynyl]benzoate (Compound 23)

Employing the same general procedure as for the preparation of ethyl 4-[(5,6,7,8-tetrahydro-8,8-dimethyl-5-(oxime)naphth-3-yl)ethynyl]benzoate (Compound 19), 1 g (2.9 mmol) of ethyl 4-[(5,6,7,8-tetrahydro-8,8-dimethyl-5-oxonaphth-2-yl)ethynyl]benzoate (Compound 1) was converted into a mixture of isomers using 1.02 g (12 mmol) of O-methyl hydroxylamine hydrochloride and 2.34 g (18 mmol) of sodium acetate trihydrate. Purification by column chromatography (silica, 5% EtOAc-hexane) gave a 6:1 ratio of the title compounds, respectively.

Ethyl 4-[(5,6,7,8-tetrahydro-8,8-dimethyl-5-anti-(O-methyl oxime)naphth-2-yl)ethynyl]benzoate (Compound 22)

PMR (CDCl$_3$): δ 1.31 (6H, s), 1.41 (3H, t, J=7.1 Hz), 1.73 (2H, t, J=6.3 Hz), 2.79 (2H, t, J=6.3 Hz), 4.02 (3H, s), 4.39 (2H, q, J=7.1 Hz), 7.36 (1H, dd, J=1.7 , 8.3 Hz), 7.54 (1H, d, J=1.7 Hz), 7.60 (2H, d, J=8.3 Hz), 7.98 (1H, d, J=8.3 Hz), 8.03 (2H, d, J=8.3 Hz).

Ethyl 4-[(5,6,7,8-tetrahydro-8,8-dimethyl-5-syn-(O-methyl oxime)naphth-2-yl)ethynyl]benzoate (Compound 23)

PMR (CDCl$_3$): δ 1.36 (6H, s), 1.42 (3H, t, J=7.1 Hz), 1.90 (2H, t, J=6.5 Hz), 2.56 (2H, t, J=6.5 HZ), 3.97 (3H, s), 4.40 (2H, q, J=7.1 Hz), 7.37 (1H, dd, J=1.5 , 8.3 Hz), 7.57 (1H, d, J=1.5 Hz), 7.61 (2H, d, J=8.6 Hz) , 8.04 (2H, d, J=8.6 Hz), 8.40 (1H, d, J=8.3 Hz).

Ethyl 4-[(5,6,7,8-tetrahydro-8,8-dimethyl-5-anti-(O-ethyl oxime)naphth-2-yl)ethynyl]benzoate (Compound 24) and Ethyl 4-[5,6,7,8-tetrahydro-8,8-dimethyl-5-syn-(O-ethyl oxime)naphth-2-yl)ethynyl]benzoate (Compound 25)

Employing the same general procedure as for the preparation of ethyl 4-[(5,6,7,8 -tetrahydro-8,8 -dimethyl-5-(oxime) naphth-3-yl)ethynyl]benzoate (Compound 19), 200 mg (0.6 mmol) of ethyl 4-[(5,6,7,8-tetrahydro-8,8-dimethyl-5-oxonaphth-2-yl)ethynyl]benzoate (Compound 1) was converted into a mixture of isomers using 185 mg (1.9 mmol) of O-ethylhydroxylamine hydrochloride and 290 mg (2.2 mmol) of sodium acetate trihydrate. Purification by column chromatography (silica, 5% EtOAc-hexane) gave a 9:1 ratio of the title compounds, respectively.

Ethyl 4-[(5,6,7,8-tetrahydro-8,8-dimethyl-5-anti-(O-ethyl oxime)naphth-2-yl)ethynyl]benzoate (Compound 24)

PMR (CDCl$_3$): δ 1.31 (6H, s), 1.35 (3H, t, J=7.1 Hz), 1.41 (3H, t, J=7.1 Hz), 1.74 (2H, t, J=6.9 Hz), 2.80 (2H, t, J=6.9 Hz), 4.27 (2H, q, J=7.1 Hz), 4.40 (2H, q, J=7.1 Hz), 7.35 (1H, dd, J=1.7 , 8.2 Hz), 7.56 (1H, d, J=1.7 Hz), 7.60 (2H, d, J=8.3 Hz), 8.00 (1H, d, J=8.2 Hz), 8.04 (2H, d, J=8.3 Hz).

Ethyl 4-[(5,6,7,8-tetrahydro-8,8-dimethyl-5-syn-(O-ethyl oxime)naphth-2-yl)ethynyl]benzoate (Compound 25)

PMR (CDCl$_3$): δ 1.35 (6H, s), 1.35 (3H, t, J=7.1 Hz), 1.42 (3H, t, J=7.1 Hz), 1.89 (2H, t, J=6.2 Hz), 2.58 (2H, t, J=6.2 Hz), 4.22 (2H, q, J=7.1 Hz), 4.40 (2H, q, J=7.1 Hz), 7.37 (1H, dd, J=1.8, 8.3 Hz), 7.58 (1H, d, J=1.8 Hz), 7.61 (2H, d, J=8.2 Hz), 8.04 (2H, d, J=8.2 Hz), 8.47 (1H, d, J=8.3 Hz).

Ethyl 4-[(5,6,7,8-tetrahydro-8,8-dimethyl-5-anti-(O-methyl oxime)naphth-3-yl)ethynyl]benzoate (Compound 26) and Ethyl 4-[(5,6,7,8-tetrahydro-8,8-dimethyl-5-syn-(O-methyl oxime)naphth-3-yl)ethynyl]benzoate (Compound 27)

Employing the same general procedure as for the preparation of ethyl 4-[(5,6,7,8-tetrahydro-8,8 -dimethyl-5-(oxime)naphth-2-yl)ethynyl]benzoate (Compound 19), 200 mg (0.6 mmol) of ethyl 4-[(5,6,7,8-tetrahydro-8,8-dimethyl-5-oxonaphth-3-yl)ethynyl]benzoate (Compound 2) was converted into a mixture of isomers using 510 mg (6 mmol) of O-methylhydroxylamine hydrochloride and 1.17 g (9 mmol) of sodium acetate trihydrate. Purification by column chromatography (silica, 5% EtOAc-hexane) followed by HPLC separation (Partisil 10, 5% EtOAc-hexane) gave a 7:1 ratio of the title compounds (t$_R$=12 minutes and 25 minutes), respectively.

Ethyl 4-[(5,6,7,8-tetrahydro-8,8-dimethyl-5-anti-(O-methyl oxime)naphth-3-yl)ethynyl]benzoate (Compound 26)

PMR (CDCl$_3$): (t$_R$=12 minutes) δ 1.28 (6H, s) , 1.41 (3H, t, J=7.1 Hz), 1.72 (2H, t, J=6.4 Hz), 2.79 (2H, t, J=6.4 Hz), 4.03 (3H, s), 4.39 (2H, q, J=7.1 Hz), 7.33 (1H, d, J=8.1 Hz), 7.46 (1H, dd, J=1.8, 8.1 Hz), 7.58 (2H, d, J=8.3 Hz), 8.03 (2H, d, J=8.3 Hz), 8.17 (1H, d, J=1.8 Hz).

Ethyl 4-[(5,6,7,8-tetrahydro-8,8-dimethyl-5-syn(O-methyl oxime)naphth-3-yl)ethynyl]benzoate (Compound 27)

PMR (acetone-d$_6$) : (t$_R$=25 minutes) δ 1.33 (6H, s), 1.34 (3H, t, J=7.1 Hz), 1.86 (2H, t, J=6.3 Hz), 2.53 (2H, t, J=6.3 Hz), 3.90 (3H, s), 4.37 (2H, q, J=7.1 Hz), 7.56 (2H, s), 7.66 (2H, d, J=8.4 Hz), 8.02 (2H, d, J=8.4 Hz), 8.57 (1H, s).

Ethyl 4-[5,6,7,8-tetrahydro-8,8-dimethyl-5-anti-(O-ethyl oxime)naphth-3-yl)ethynyl]benzoate (Compound 28) and Ethyl 4-[5,6,7,8-tetrahydro-8,8,dimethyl-5-syn-(O-ethyl oxime)naphth-3-yl)ethynyl]benzoate (Compound 29)

Employing the same general procedure as for the preparation of ethyl 4-[(5,6,7,8-tetrahydro-8,8-dimethyl-5-(oxime) naphth-3-yl)ethynyl]benzoate (Compound 19), 200 mg (0.6 mmol) of ethyl 4-[(5,6,7,8-tetrahydro-8,8-dimethyl-5-oxonaphth-3yl)ethynyl]benzoate (Compound 2) was converted into a mixture of isomers using 185 mg (1.9 mmol) of O-ethylhydroxylamine hydrochloride and 290 mg (2.2 mmol) of sodium acetate trihydrate. Purification by column chromatography (silica, 5% EtOAc-hexane) followed by HPLC separation (Partisil 10, 5% EtOAc-hexane) gave a 6.6:1 ratio of the title compounds ($t_R$=15 minutes and 20 minutes), respectively.

Ethyl 4-[(5,6,7,8-tetrahydro-8,8-dimethyl-5-anti-(O-ethyl oxime)naphth-3-yl)ethynyl]benzoate (Compound 28)

PMR (CDCl$_3$) : ($t_R$=15 minutes) δ 1.30 (6H, s) , 1.36 (3H, t, J=7.1 Hz), 1.41 (3H, t, J=7.1 Hz), 1.73 (2H, t, J=7.0 Hz), 2.81 (2H, t, J=7.0 Hz), 4.28 (2H, q, J=7.1 Hz), 4.40 (2H, q, J=7.1 Hz), 7.34 (1H, d, J=8.2 Hz), 7.46 (1H, dd, J=1.8, 8.2 Hz), 7.59 (2H, d, J=8.6 Hz), 8.02 (2H, d, J=8.6 Hz), 8.17 (1H, d, J=1.8 Hz).

Ethyl 4-[5,6,7,8-tetrahydro-8,8-dimethyl-5-syn-(O-ethyl oxime)naphth-3-yl)ethynyl]benzoate (Compound 29)

PMR (acetone-d$_6$) : ($t_R$=20 minutes) δ 1.30 (3H, t, J=7.1 Hz), 1.33 (6H, s), 1.37 (3H, t, J=7.1 Hz), 1.86 (2H, t, J=6.3 Hz), 2.53 (2H, t, J=6.3 Hz), 4.16 (2H, q, J=7.1 Hz), 4.35 (2H, q, J=7.1 Hz), 7.56 (2H, s), 7.66 (2H, d, J=7.6 Hz), 8.03 (2H, d, J=7.6 Hz), 8.65 (1H, s).

Ethyl 4-[(5,6,7,8-tetrahydro-8,8-dimethyl-5-anti-(O-(2-tetrahydropyranyl) oxime)naphth-3-yl)ethynyl]benzoate (Compound 30)

200 mg (0.55 mmol) of ethyl 4-[(5,6,7,8-tetra-hydro-8,8-dimethyl-5-(oxime)naphth-3-yl)ethynyl]benzoate (Compound 19) was added to CH$_2$Cl$_2$ and stirred at ambient temperature for approximately 16 hours with 84 mg (1 mmol) of 3,4-dihydro-2H-pyran and 14 mg (0.06 mmol) of pyridinium p-toluenesulfonate. Thereafter, K$_2$CO$_3$ was added, the organic solution washed with water and brine and dried (MgSO$_4$). The products were isolated by chromatography.

PMR (CDCl$_3$): δ 1.29 (3H, s), 1.30 (3H, s), 1.40 (3H, t, J=7.1 Hz), 1.55–1.70 (4H, m), 1.75 (2H, t, J=6.0 Hz), 1.80–1.92 (2H, m), 2.80–3.00 (2H, m), 3.55–3.72 (1H, m), 3.90–4.00 (1H, m), 4.38 (2H, q, J=7.1 Hz), 5.44 (1H, t, J=4.6 Hz), 7.33 (1H, d, J=7.8 Hz), 7.46 (1H, dd, J=1.9, 7.8 Hz), 7.57 (2H, d, J=8.1 Hz), 8.01 (2H, d, J=8.1 Hz), 8.24 (1H, d, J=1.9 Hz).

Ethyl 4-[(5,6,7,8-tetrahydro-8,8-dimethyl-5-anti-(O-(2-tetrahydropyranyl) oxime)naphth-2-yl)ethynyl]benzoate (Compound 31)

Employing the same general procedure as for the preparation of ethyl 4-[(5,6,7,8-tetrahydro-8,8-dimethyl -5-anti-(O-(2-tetrahydropyranyl) oxime)naphth-3-yl)ethynyl]benzoate (Compound 30), 346 mg (1 mmol) of ethyl 4-[(5,6,7, 8-tetrahydro-8,8-dimethyl-5-(oxime)naphth-2-yl)ethynyl] benzoate (Compound 20) was converted into the title compound using 420 mg (5 mmol) of 3,4-dihydro-2H-pyran and 10 mg (0.04 mmol) of pyridinium p-toluenesulfonate.

PMR (CDCl$_3$): δ 1.32 (3H, s), 1.33 (3H, s), 1.41 (3H, t, J=7.1 Hz), 1.56–1.70 (3H, m), 1.75 (2H, t, J=6.0 Hz), 1.80–1.95 (3H, m), 2.80–3.05 (2H, m), 3.65–3.74 (1H, m), 3.90–4.00 (1H, m), 4.40 (2H, q, J=7.1 Hz), 5.42 (1H, t, J=3.0 Hz), 7.34 (1H, dd, J=1.9, 8.0 Hz), 7.53 (1H, d, J=1.9 Hz), 7.60 (2H, d, J=8.2 Hz), 8.03 (2H, d, J=8.2 Hz), 8.06 (1H, d, J=8.0 Hz).

4-[5,6,7,8-tetrahydro-8,8-dimethyl-5-anti-(O-(2-tetrahydropyranyl) oxime)naphth-3-yl)ethynyl]benzoic acid (Compound 38)

124 mg (0.34 mmol) of ethyl 4-[(5,6,7,8-tetrahydro-8,8-dimethyl-5-anti-(O-(2-tetrahydropyranyl) oxime) naphth-3-yl) ethynyl]benzoate (Compound 30) in a mixture of THF and methanol was refluxed (2 hours) with 1 ml (1 mmol) of LiOH (1M aqueous solution). Thereafter the mixture was diluted with Et$_2$O:EtOAc (1:1), and acidified with aqueous HCl to pH5. The organic phase was separated, washed (water and brine) and dried (MgSO$_4$) to yield the title compound.

PMR (DMSO-d$_6$): δ 1.25 (6H, s), 1.50–1.80 (8H, m), 2.65–2.90 (2H, m), 3.50–3.60 (1H, m), 3.70–3.80 (1H, m), 5.36 (1H, br s), 7.49 (1H, d, J=8.0 Hz), 7.56 (1H, dd, J=1.9, 8.0 Hz), 7.68 (2H, d, J=8.2 Hz), 7.94 (2H, d, J=8.2 Hz), 8.01 (1H, d, J=1.9 Hz).

4-[(5,6,7,8-tetrahydro-8,8-dimethyl-5-anti-(O-(2-tetrahydropyranyl) oxime)naphth-2-yl)ethynyl]benzoic acid (Compound 39)

Employing the same general procedure as for the preparation of 4-[(5,6,7,8-tetrahydro-8,8-dimethyl-5-anti-(O-(2-tetrahydropyranyl) oxime)naphth-3-yl)ethynyl]benzoic acid (Compound 38), 160 mg (0.37 mmol ) of ethyl 4-[(5,6,7,8-tetrahydro-8,8-dimethyl-5-anti-(O-(2-tetrahydropyranyl) oxime) naphth-2-yl)ethynyl]benzoate (Compound 31) was converted into the title compound using 1 ml (1 mmol) of LiOH (1M aqueous solution).

PMR (CDCl$_3$): δ 1.32 (3H, s), 1.33 (3H, s), 1.56–1.95 (8H, m), 2.78–3.02 (2H, m), 3.65–3.75 (1H, m), 3.93–4.02 (1H, m), 5.45 (1H, br s), 7.31 (1H, dd, J=1.5, 8.1 Hz), 7.53 (1H, d, J=1.5 Hz), 7.62 (2H, d, J=8.2 HZ), 8.04 (1H, d, J=8.1 HZ), 8.06 (2H, d, J=8.2 Hz).

4-[(5,6,7,8-tetrahydro-8,8-dimethyl-5-(oxime)naphth-3-yl)ethynyl]benzoic acid (Compound 46)

217 mg (0.6 mmol) of ethyl 4-[(5,6,7,8-tetrahydro-8,8-dimethyl-5-(oxime)naphth-3-yl)ethynyl]benzoate (Compound 19) dissolved in a mixture of THF and methanol was converted into the title compound using 2 ml (2 mmol) of LiOH (1M aqueous solution) by refluxing for approximately 2 hours.

PMR (CD$_3$OD): δ 1.30 (6H, s) , 1.74 (2H, t, J=7.0 Hz), 2.82 (2H, t, J=7.0 Hz), 4.92 (1H, br s), 7.41–7.48 (2H, m), 7.60 (2H, d, J=8.2 Hz), 8.02 (2H, d, J=8.2 Hz), 8.06 (1H, d, J=1.5 Hz).

4-[5,6,7,8-tetrahydro-8,8-dimethyl-5-(oxime)naphth-2-yl)ethynyl]benzoic acid (Compound 47)

Employing the same general procedure as for the preparation of 4-[(5,6,7,8-tetrahydro-8,8-dimethyl-5-(oxime)naphth-3-yl)ethynyl]benzoic acid (Compound 46), 150 mg (0.4 mmol) of ethyl 4-[(5,6,7,8-tetrahydro-8,8-dimethyl-5-(oxime)naphth-2-yl)ethynyl]benzoate (Compound 20) was converted into the title compound using 2 ml (2 mmol) of LiOH (1M aqueous solution).

PMR (CD$_3$OD): δ 1.11 (6H, s), 1.54 (2H, t, J=6.0 Hz), 2.62 (2H, t, J=6.0 Hz), 7.10 (1H, d, J=8.2 Hz), 7.31 (2H, d, J=6.8 Hz), 7.33 (1H, s), 7.70 (1H, d, J=8.2 Hz), 7.78 (2H, d, J=6.8 Hz).

6-[(5,6,7,8-tetrahydro-8,8-dimethyl-5-(oxime)naphth-2-yl)ethynyl]nicotinic acid (Compound 48)

Employing the same general procedure as for the preparation of 4-[(5,6,7,8-tetrahydro-8,8-dimethyl-5-(oxime)naphth-3-yl)ethynyl]benzoic acid (Compound 46), 36 mg (0.1 mmol) of ethyl 6-[(5,6,7,8-tetrahydro-8,8-dimethyl-5-(oxime)naphth-2-yl)ethynyl]nicotinate (Compound 21) was converted into the title compound using 0.5 ml (0.5 mmol) of LiOH (1M aqueous solution).

PMR (acetone-d$_6$) : δ 1.33 (6H, s), 1.76 (2H, t, J=6.8 Hz), 2.85 (2H, t, J=6.8 Hz), 7.41 (1H, d, J=8.1 Hz), 7.68 (1H, s), 7.74 (1H, d, J=8.1 Hz), 8.00 (1H, d, J=8.2 Hz), 8.35 (1H, d, J=8.2 Hz), 9.16 (1H, s).

4-[(5,6,7,8-tetrahydro-8,8-dimethyl-5-anti-(O-methyl oxime)naphth-2-yl)ethynyl]benzoic acid (Compound 49)

Employing the same general procedure as for the preparation of 4-[(5,6,7,8-tetrahydro-8,8-dimethyl-5-(oxime)naphth-3-yl) ethynyl]benzoic acid (Compound 46), 130 mg (0.35 mmol) of ethyl 4-[(5,6,7,8-tetrahydro-8,8-dimethyl-5-anti-(O-methyl oxime) naphth-2-yl)ethynyl]benzoate (Compound 22) was converted into the title compound using 1 ml (1.0 mmol) of LiOH (1M aqueous solution).

PMR (CDCl$_3$): δ 1.32 (6H, s), 1.74 (2H, t, J=6.3 Hz), 2.79 (2H, t, J=6.3 Hz), 4.03 (3H, s), 7.38 (1H, dd, J=1.7, 8.3 Hz), 7.55 (1H, d, J=1.7 Hz), 7.64 (2H, d, J=8.4 Hz), 7.99 (1H, d, J=8.3 Hz), 8.10 (2H, d, J=8.4 Hz).

4-[(5,6,7,8-tetrahydro-8,8-dimethyl-5-syn-(O-methyl oxime) naphth-3-yl)ethynyl]benzoic acid (Compound 50)

Employing the same general procedure as for the preparation of 4-[(5,6,7,8-tetrahydro-8,8-dimethyl-5-(oxime)naphth-3-yl)ethynyl]benzoic acid (Compound 46), 40 mg (0.15 mmol) of ethyl 4-[(5,6,7,8-tetrahydro-8,8-dimethyl-5-syn-(O-methyl oxime)naphth-3-yl)ethynyl]benzoate (Compound 23) was converted into the title compound using 0.5 ml (0.5 mmol) of LiOH (1M aqueous solution). PMR (CDCl$_3$): δ 1.36 (6H, s), 1.90 (2H, t, J=6.3 Hz), 2.58 (2H, t, J=6.3 Hz), 3.97 (3H, s), 7.38 (1H, d, J=8.3 Hz), 7.59 (1H, s), 7.65 (2H, d, J=8.3 Hz), 8.10 (2H, d, J=8.3 Hz), 8.41 (1H, d, J=8.3 Hz).

4-[(5,6,7,8-tetrahydro-8,8-dimethyl-5-anti-(O-ethyl oxime)naphth-2-yl)ethynyl]benzoic acid (Compound 51)

Employing the same general procedure as for the preparation of 4-[(5,6,7,8-tetrahydro-8,8-dimethyl-5-(oxime)naphth-3-yl)ethynyl]benzoic acid (Compound 46), 40 mg (0.15 mmol) of ethyl 4-[(5,6,7,8-tetrahydro-8,8-dimethyl-5-anti-(O-ethyl oxime) naphth-2-yl)ethynyl]benzoate (Compound 24) was converted into the title compound using 0.5 ml (0.5 mmol) of LiOH (1M aqueous solution).

PMR (CDCl$_3$): δ 1.32 (6H, s), 1.36 (3H, t, J=7.1 Hz), 1.74 (2H, t, J=6.4 Hz), 2.82 (2H, t, J=6.4 Hz), 4.27 (2H, q, J=7.1 Hz), 7.37 (1H, dd, J=1.6, 8.2 Hz), 7.55 (1H, d, J=1.6 Hz), 7.64 (2H, d, J=8.4 Hz), 8.01 (1H, d, J =8.2 Hz), 8.11 (2H, d, J =8.4 Hz).

4-[(5,6,7,8-tetrahydro-8,8-dimethyl-5-syn-(O-ethyl oxime)naphth-2-yl)ethynyl]benzoic acid (Compound 52)

Employing the same general procedure as for the preparation of 4-[(5,6,7,8-tetrahydro-8,8-dimethyl-5-(oxime)naphth-3-yl)ethynyl]benzoic acid (Compound 46), 10 mg (0.03 mmol) of ethyl 4-[(5,6,7,8-tetrahydro-8,8-dimethyl-5-syn-(O-ethyl oxime)naphth-2-yl)ethynyl]benzoate (Compound 25) was converted into the title compound using 1 ml (1.0 mmol) of LiOH (1M aqueous solution).

PMR (CDCl$_3$): δ 1.31 (6H, s), 1.35 (3H, t, J=7.1 Hz), 1.74 (2H, t, J=6.9 Hz), 2.80 (2H, t, J=6.9 Hz), 4.27 (2H, q, J=7.1 Hz), 7.35 (1H, d, J=8.3 Hz), 7.59 (1H, s), 7.65 (2H, d, J=8.3 Hz), 8.10 (2H, d, J=8.3 Hz), 8.41 (1H, d, J=8.3 Hz).

4-[(5,6,7,8-tetrahydro-8,8-dimethyl-5-anti-(O-methyl oxime)naphth-3-yl)ethynyl]benzoic acid (Compound 53)

Employing the same general procedure as for the preparation of 4-[(5,6,7,8-tetrahydro-8,8-dimethyl-5-(oxime)naphth-3-yl)ethynyl]benzoic acid (Compound 46), 85 mg (0.23mmol) of ethyl 4-[(5,6,7,8-tetrahydro-8,8-dimethyl-5-anti-(O-methyl oxime) naphth-3-yl)ethynyl]benzoate ( Compound 26) was converted into the title compound using 1 ml (1.0 mmol) of LiOH (1M aqueous solution).

PMR (acetone-d$_6$) : δ 1.31 (6H, s), 1.74 (2H, t, J=6.3 Hz), 2.80 (2H, t, J=6.3 Hz), 4.04 (3H, s), 7.36 (1H, d, J=8.2 Hz), 7.48 (1H, dd, J=1.8 , 8.2 Hz), 7.62 (2H, d, J=8.3 Hz), 8.10 (2H, d, J=8.3 Hz), 8.17 (1H, d, J=1.8 Hz).

4-[(5,6,7,8-tetrahydro-8,8-dimethyl-5-syn-(O-methyl oxime)naphth-3-yl)ethynyl]benzoic acid (Compound 54)

Employing the same general procedure as for the preparation of 4-[(5,6,7,8-tetrahydro-8,8-dimethyl-5-(oxime)naphth-3-yl)ethynyl]benzoic acid (Compound 46), 20 mg (0.05 mmol) of ethyl 4-[(5,6,7,8-tetrahydro-8,8-dimethyl-5-syn-(O-methyl oxime) naphth-2-yl)ethynyl]benzoate (Compound 27) was converted into the title compound using 0.2 ml (0.2 mmol) of LiOH (1M aqueous solution).

PMR (acetone-d$_6$) : δ 1.34 (6H, s) , 1.87 (2H, t, J=6.3 Hz), 2.53 (2H, t, J=6.3 Hz), 3.90 (3H, s), 7.57 (2H, s) , 7.67 (2H, d, J=8.2 Hz), 8.06 (2H, d, J=8.2 Hz), 8.57 (1H, s).

4-[(5,6,7,8-tetrahydro-8,8-dimethyl-5-anti-(O-ethyl oxime)naphth-3-yl)ethynyl]benzoic acid (Compound 55)

Employing the same general procedure as for the preparation of 4-[(5,6,7,8-tetrahydro-8,8-dimethyl-5-(oxime)naphth-3-yl)ethynyl]benzoic acid (Compound 46), 80 mg (0.21 mmol) of ethyl 4-[(5,6,7,8-tetrahydro-8,8-dimethyl-5-anti-(O-ethyl oxime) naphth-3-yl)ethynyl]benzoate (Compound 26) was converted into the title compound using 0.6 ml (0.6 mmol) of LiOH (1M aqueous solution).

PMR (CDCl$_3$): δ 1.31 (6H, s), 1.37 (3H, t, J=7.1 Hz), 1.74 (2H, t, J=6.8 Hz), 2.81 (2H, t, J=6.8 Hz), 4.28 (2H, q, J=7.1 Hz), 7.35 (1H, d, J=8.2 Hz), 7.47 (1H, dd, J=1.7, 8.2 Hz), 7.63 (2H, d, J=8.4 Hz), 8.10 (2H, d, J=8.4 Hz), 8.18 (1H, d, J=1.7 Hz).

What is claimed is:

1. A compound of the formula

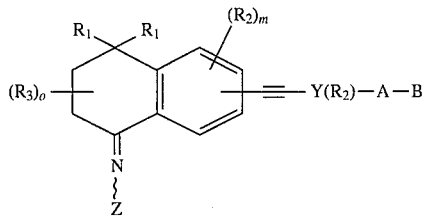

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the tetrahydronaphthalene ring;

m is an integer having the value of 0–3;

o is an integer having the value 0–4;

Y is phenyl optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}$, or tri-lower alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; the wavy line represents a single valence bond around which the configuration can be syn or anti, and Z is $OR_1$, $R_1$ phenyl, benzyl, lower alkyl or lower alkoxy substituted phenyl, $OSi(R_2)_3$, $OCOR_{14}$, $OC(R_{15})(R_{16})XR_{17}$, $N(R_{14})_2$, $NHCON(R_{14})_2$, $NHCSN(R_{14})_2$, where X is O or S; $R_{14}$ is hydrogen, alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1$-$C_{10}$-alkylphenyl, naphthyl, $C_1$-$C_{10}$-alkylnaphthyl, phenyl-$C_1$-$C_{10}$alkyl, naphthyl-$C_1$-$C_{10}$alkyl; $R_{15}$ and $R_{16}$ are hydrogen or lower alkyl of 1 to 6 carbons, and $R_{17}$ is lower alkyl of 1 to 6 carbons.

2. A compound of claim 1 where the phenyl ring is 1,4 (para) substituted.

3. A compound of claim 1 where $R_2$ is hydrogen.

4. A compound of claim 1 where $R_3$ is hydrogen.

5. A compound of claim 1 where Z is $OR_1$ or $OC(R_{15})(R_{16}) XR_{17}$.

6. A compound of claim 5 where Z is OH, $OCH_3$, $OCH_2CH_3$, or $OCH_2OCH_3$.

7. A compound of the formula

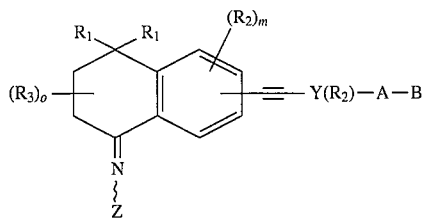

wherein $R_1$ is hydrogen or alkyl of 1 to 10 carbons;

$R_2$ and $R_3$ are hydrogen, or alkyl of 1 to 6 carbons and the substituted ethynyl group occupies either the 2 or the 3 position of the tetrahydronaphthalene ring;

m is an integer having the value of 0–3;

o is an integer having the value 0–4;

Y is phenyl optionally substituted with one or two $R_2$ groups;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or tri-lower alkylsilyl, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons; the wavy line represents a single valence bond around which the configuration can be syn or anti, and Z is $OR_1$, $OC(R_{15})(R_{16})XR_{17}$, where X is O or S; $R_{15}$ and $R_{16}$ are hydrogen or lower alkyl of 1 to 6 carbons, and $R_{17}$ is lower alkyl of 1 to 6 carbons.

8. A compound of claim 7 where A is $(CH_2)_n$ where n is 0–5 and where B is COOH or a pharmaceutically acceptable salt thereof, $COOR_8$, or $CONR_9R_{10}$.

9. A compound of claim 8 where Z is OH, $OCH_3$, or $OCH_2CH_3$.

10. A compound of the formula

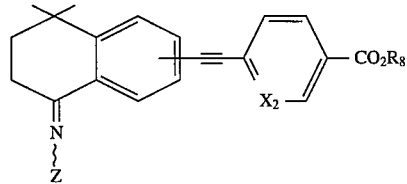

wherein $X_2$ is CH;

$R_8$ is hydrogen, an alkyl group of 1 to 10 carbons or (trimethylsilyl)alkyl where the alkyl group has 1 to 10 carbons, the substituted ethynyl group occupies either the 2 or 3 position of the tetrahydronaphthalene ring, and Z is $OR_1$, $OC(R_{15})(R_{16})XR_{17}$, where X is O or S; $R_1$ is H or lower alkyl, $R_{15}$ and $R_{16}$ are hydrogen or lower alkyl, and $R_{17}$ is lower alkyl.

11. A compound of claim 10 where Z is OH.
12. A compound of claim 11 where $R_8$ is H or $C_2H_5$.
13. A compound of claim 10 where Z is $OCH_3$.
14. A compound of claim 13 where $R_8$ is H or $C_2H_5$.
15. A compound of claim 10 where Z is $OCH_2CH_3$.
16. A compound of claim 15 where $R_8$ is H or $C_2H_5$.

* * * * *

UNITED STATES PATENT AND TRADEMARK OFFICE
CERTIFICATE OF CORRECTION

PATENT NO. : 5,599,967
DATED : February 4, 1997
INVENTOR(S) : Vuligonda et al.

It is certified that error appears in the above-indentified patent and that said Letters Patent is hereby corrected as shown below:

Column 6, lines 36-37, "substititutions" should be --substitutions--.

Column 8, line 55, after "$IC_{60}$", add --"--.

Column 15, line 62, after "of", delete "of".

Column 19, line 55, after "(3H,t,J-6.2 Hz)", add --,--.

Column 20, line 15, after "1-93-dimethylamino", delete "-".

Signed and Sealed this

Sixteenth Day of December, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,599,967
DATED : February 4, 1997
INVENTOR(S) : Vuligonda et al.

It is certified that error appears in the above-indentified patent and that said Letters Patent is hereby corrected as shown below:

Column 1, line 62 after "T-Cell", delete "Cell".

Column 2 line 59, "$CHOR_{13}$" should be --$CHOR_{13}O$--.

Column 14, line 16, after "4-dimethylnaphthalen-1(2H) add -- - --.

Column 14, line 20, change "Z" to --2--.

Column 18, line 57, after "6-Ethynyl", delete "," and add -- - --.

Column 19, line 23, after "6-ethynyl-3,4-dihydro-4,4-dimethyl", delete "-".

Column 21, line 8, after "6", add -- - --.

Column 21, line 23, change "HZ" to --Hz--.

Column 21, line 27, should read "6-[(5,6,7,8-tetrahydro-8,8-dimethyl-5-oxonaphth-2- --.

Column 21, line 44, after "4-[", add --(--.

Column 21, line 63, after "oxonaphth-3", add -- - --.

Column 22, line 12, after "4-[", add --(--.

UNITED STATES PATENT AND TRADEMARK OFFICE
CERTIFICATE OF CORRECTION

PATENT NO. : 5,599,967
DATED : February 4, 1997
INVENTOR(S) : Vuligonda et al.

It is certified that error appears in the above-indentified patent and that said Letters Patent is hereby corrected as shown below:

Column 22, line 33, after "4-[", add--(--.

Column 22, line 52, after "6-[", add --(--.

Column 23, line 38, change "HZ" to --Hz--.

Column 23, line44, after "4-[", add --(--.

Column 24, line 44, after "4-[(5,6,7,8-tetrahydro-8,8-dimethyl-5-syn", add -- - --.

Column 24, line 54, after "4-[", add --(--.

Column 24, line 57, after "4-[", add --(--.

Column 24, line 64, after "5-oxonaphth-3", add -- - --.

Column 25, line 19, after "4-[", add --(--.

Column 26, line 6, after "4-[", add --(--.

Column 26, line 42, change "HZ" to --Hz--.

Column 26, line 43, change "HZ" to --Hz--.

Column 26, line 58, after "4-[", add --(--.

Column 27, line 20, after "4-[(5,6,7,8-tetrahydro-8", delete "." and add --,--.

UNITED STATES PATENT AND TRADEMARK OFFICE
CERTIFICATE OF CORRECTION

PATENT NO. : 5,599,967
DATED : February 4, 1997
INVENTOR(S) : Vuligonda et al.

It is certified that error appears in the above-indentified patent and that said Letters Patent is hereby corrected as shown below:

Column 29, line 32, "$CR_7OR_{13}$" should be --$CR_7OR_{13}O$--.

Signed and Sealed this

Seventeenth Day of March, 1998

*Attest:*

*Attesting Officer*

BRUCE LEHMAN

*Commissioner of Patents and Trademarks*